United States Patent
Voigt et al.

(10) Patent No.: US 7,056,554 B2
(45) Date of Patent: Jun. 6, 2006

(54) PRODUCTION OF POLYELECTROLYTE CAPSULES BY SURFACE PRECIPITATION

(75) Inventors: Andreas Voigt, Berlin (DE); Gleb Sukhorukov, Potsdam (DE); Igor Radtchenko, Yaroslavl (RU); Alexei Antipov, Moskau (RU); Edwin Donath, Giesenhorst (DE); Helmuth Möhwald, Bingen (DE)

(73) Assignee: Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 180 days.

(21) Appl. No.: 10/343,670

(22) PCT Filed: Aug. 1, 2001

(86) PCT No.: PCT/EP01/08909

§ 371 (c)(1),
(2), (4) Date: Feb. 3, 2003

(87) PCT Pub. No.: WO02/09865

PCT Pub. Date: Feb. 7, 2002

(65) Prior Publication Data

US 2003/0175517 A1    Sep. 18, 2003

(30) Foreign Application Priority Data

Aug. 2, 2000   (DE) ............................ 100 37 707
Oct. 11, 2000  (DE) ............................ 100 50 382

(51) Int. Cl.
    *B05D 7/02*    (2006.01)
    *B01J 13/22*   (2006.01)

(52) U.S. Cl. .............................. 427/213.3; 427/207.1; 427/212; 427/213.31; 427/213.36; 427/220; 427/340; 424/489

(58) Field of Classification Search ............ 427/207.1, 427/212, 213.3, 213.31, 213.36, 220, 340; 424/489
See application file for complete search history.

(56) References Cited

FOREIGN PATENT DOCUMENTS

| EP | 0 972 563 | | 1/2000 |
|---|---|---|---|
| EP | 1 116 516 | | 7/2001 |
| EP | 1116516 | * | 7/2001 |
| WO | WO 99 47253 | | 9/1999 |
| WO | WO 99/47253 | * | 9/1999 |
| WO | WO 01 64330 | | 9/2001 |

* cited by examiner

*Primary Examiner*—Samuel A. Acquah (74) *Attorney, Agent, or Firm*—Sutherland Asbill & Brennan LLP (57) ABSTRACT

The invention concerns a method for producing nanocapsules and microcapsules comprising a polyelectrolyte shell by surface precipitation from the solution, by applying a shell to template particles comprising the steps (a) providing a dispersion of template particles of suitable size in a salt-containing liquid phase which contains the components required to form the shell in a dissolved form and (b) precipitating the components from the liquid phase onto the template particles under conditions which enable the formation of a shell around the template particles that has a thickness of from 1 to 100 nm.

26 Claims, 8 Drawing Sheets

PRODUCTION OF POLYELECTROLYTE CAPSULES BY SURFACE PRECIPITATION

DESCRIPTION

The invention concerns a method for producing nanocapsules and microcapsules comprising a polyelectrolyte shell by surface precipitation from the solution.

DE 198 12 083.4, DE 199 07 552.2, EP 98 113 181.6 and WO 99/47252 disclose a method for producing capsules coated with a polyelectrolyte shell by applying polyelectrolytes in layers on template particles. An advantage of this method over earlier methods for producing microcapsules is that it enables the production of monodisperse capsules having a defined wall thickness. However, a problem from an economical perspective is that the construction of a capsule shell in layers can be time-consuming and laborious.

Buchhammer and Lunkwitz (Ber. Bunsenges Phys. Chem. 100 (1996), 1039–1044) and Oertel et al. (Coll. Surf. 57 (1991), 375–381) describe the surface modification of organic and inorganic particles by depositing a complex of positively and negatively charged polyelectrolytes on the particle surface. A disadvantage of this method is that the resulting layers have a poor stability.

Hence one object of the invention was to provide a new method for producing capsules of high stability and shells having a low wall thickness in which the disadvantages of the prior art are at least partially eliminated.

This object is achieved by a method for applying a shell to template particles by means of surface precipitation from a solution wherein this method comprises the following steps:
(a) providing a dispersion of template particles of suitable size in a salt-containing liquid phase which contains the components required to form the shell in a dissolved form and
(b) precipitating the components from the liquid phase onto the template particles under conditions which enable the formation of a shell around the template particles that has a thickness of from 1 to 100 nm.

It was surprisingly found that it is possible to obtain capsules having a defined and low shell thickness and selectively controllable permeability properties by coating template particles by surface precipitation from a salt-containing solution. This method enables the formation of various types of shells e.g. polyelectrolyte shells, polyelectrolyte/ion shells and also shells consisting of uncharged polymers.

The salts dissolved in the liquid make a substantial contribution to the stability of the shells formed by precipitation. Examples of suitable salts are all water-soluble low molecular salts including inorganic salts such as chlorides, bromides, nitrates, sulphates and carbonates of monovalent and polyvalent alkaline, alkaline earth or transition metals such as iron, silver and copper. The concentrations are preferably in the range of 0.5 mM to 1 M, or higher in cases in which the effect of the salt is to reduce the electrostatic interaction between polyelectrolytes on the one hand and the polyelectrolytes and the template surfaces on the other hand. If a specific interaction and/or complexing of polyvalent low molecular anions and cations with the polyelectrolytes is necessary in order to produce dispersed polyelectrolyte pools in the shell liquid, the concentrations of the salts are preferably in the range from 0.001 to 10 mM.

The encapsulation method according to the invention enables the encapsulation of any colloidal particles. In addition to solid particles, it is also possible to coat liquid particles e.g. emulsified oil droplets or liquid-crystalline particles or gaseous particles e.g. air bubbles or other gas bubbles. The size of the liquid or gas particles to be encapsulated can for example be adjusted by adding surface-active agents to the liquid phase.

Any colloidal solids can be used as solid template particles and in particular inorganic materials e.g. metals, ceramics, oxides or salt crystals, organic materials such as polymer latices, organic precipitates, solidified oil droplets, gels or crystals, melamine-formaldehyde particles, lipid vesicles, biological template particles such as cells or pollen. The size of the template particles can be up to 50 μm—especially when using biological template materials. However, the size of the template particles is preferably up to 10 μm, particularly preferably 5 nm to 10 μm and most preferably 5 nm to 5 μm. The shape of the template particles is not critical. Spherical as well as anisotropic particles can be coated.

In a preferred embodiment template particles are encapsulated which contain an active substance e.g. which themselves constitute an active substance. This active substance can for example be selected from catalysts, in particular enzymes e.g. enzyme crystals, nanoparticles e.g. magnetic nanoparticles, biological macromolecules etc., pharmaceutical agents, sensor molecules e.g. radioactive or non-radioactive labelling molecules such as fluorescent labels, crystals, polymers and gases. The particles of active substance can be added to the liquid phase or be generated therein by precipitation. The precipitation can occur before or/and during the capsule formation and result in crystals or/and amorphous structures.

The capsules can for example be used to introduce organic liquids such as alcohols or hydrocarbons e.g. hexanol, octanol, octane or decane or to encapsulate gases for ultrasonic contrast agents. Such capsules filled with an organic liquid that is not miscible with water can also be used for chemical reactions e.g. polymerization reactions. In this manner it is possible to concentrate the monomer in the interior of the capsules by means of its distribution equilibrium. The monomer solution may already be encapsulated in the interior before the start of the synthesis.

However, it is also possible to encapsulate active substances which cannot penetrate through the polyelectrolyte shell due to their size. For this purpose the active substance to be incorporated is coupled to or immobilized on the template particle or encapsulated or taken up by the template particle e.g. by phagocytosis or endocytosis in the case of living cells or by encapsulation of nanoparticles in soluble template materials. After the template particle has disintegrated the active substance is released into the interior of the polyelectrolyte shell. The conditions for the disintegration of template particles are expediently selected such that no undesired decomposition of the active substance occurs.

The active substance can be directly coupled to the template or by means of a binding mediator. Molecules which can be degraded or decomposed under particular conditions are preferably used as binding mediators. Polylactic acid is preferably used as the binding mediator. In this case the active substance is immobilized by means of the binding mediator, in particular polylactic acid, on the template particle which is for example a partially cross-linked melamine-formaldehyde particle. In this manner the active substance to be encapsulated becomes a component of the layer structure in the core coating. After dissolution of the template particles and optionally degradation of the binding molecules, the active substance is released into the interior of the shell. This method enables any active substances to be enclosed in the shell, in particular nanoparticles and non-biological macromolecular components and preferably biological macromolecules such as proteins and especially enzymes.

Furthermore cationic polymers or particles can be immobilized in the shell by for example using 4-pyrene sulfate (4-PS). These particles are then released into the interior of the shell by dissolving out 4 PS in salt solutions.

Active substances can be incorporated in the inner space enclosed by the shells by prior incorporation of the active substances into the template particles when reversible microgels are used as the template particles. Thus for example use of partly cross-linked methylol-melamine cores before the coating enables the incorporation of substances into swollen cores, which are enclosed in the core after a reversible shrinking.

In another preferred embodiment of the method according to the invention soluble particles can be used as template particles. These soluble particles can be at least partially disintegrated without destroying the shell formed around the particles by precipitation. Examples of soluble particles are partly cross-linked melamine-formaldehyde particles that can be dissolved by adjusting the pH in the medium containing the coated particles to an acidic value e.g. $\leq 1.5$, during which the shell layer remains at least partly intact. Partly cross-linked melamine-formaldehyde particles can also be dissolved by chemical reactions especially by sulfonation in aqueous media. The production of such partly cross-linked melamine-formaldehyde particles is described in detail in WO 99/47252. Other examples of dissolvable template particles are soluble polymer cores e.g. urea formaldehyde particles or salt crystals, or salt crystals e.g. carbonate compounds whose solubility in aqueous solutions can be adjusted or organic compounds that are insoluble in water but soluble in ethanol e.g. cyanine dyes.

Other template materials that can be used are for example cells, e.g. eukaryotic cells such as mammalian erythrocytes or plant cells, monocellular organisms such as yeasts, bacterial cells such as *E. coli* cells, cell aggregates, subcellular particles such as cell organelles, pollen, membrane precipitations or cell nuclei, or hollow cell wall or pollen wall preparations produced by chemical or/and biological methods, virus particles and aggregates of biomolecules e.g. protein aggregates such as immune complexes, condensed nucleic acids, ligand-receptor complexes etc. The method according to the invention is also suitable for encapsulating living biological cells and organisms. Other suitable templates are aggregates of amphiphilic materials, in particular membrane structures such as vesicles e.g. liposomes or micelles and other lipid aggregates.

Biological template particles can be disintegrated by adding lysis reagents. Suitable lysis reagents are those which can dissolve biological materials such as proteins or/and lipids. The lysis reagents preferably contain a deproteinization agent for example peroxo compounds such as $H_2O_2$ or/and hypochlorite compounds such as sodium or potassium hypochlorite. Surprisingly the template particles disintegrate within a short incubation period e.g. 1 min to 1 h at room temperature. The disintegration of the template particles is substantially complete since remnants of the particles are no longer detectable even when the remaining shells are observed under an electron microscope. When biological materials are incorporated into the shell it is possible to produce capsules with partly dissolved shells.

The fragments formed when the template particles disintegrate e.g. the oligomers formed when partly cross-linked melamine-formaldehyde particles disintegrate, can escape from the inside of the capsules through pores especially nanopores of the shell wall. They can be subsequently separated from the capsules if desired. This separation can be carried out by methods known to a person skilled in the art e.g. by dialysis, filtration, centrifugation or/and controlled phase separation. However, it is often unnecessary to separate template particle fragments. The capsules can also be used without a separation step.

Moreover it is also possible to use liquid or gaseous template particles e.g. drops of a microemulsion or miniemulsion or gas bubbles of an appropriate size. Oil drops are particularly preferably used as liquid template particles which can be emulsified by ultrasound in an aqueous salt-containing solution. The size of the liquid droplets or gas bubbles can be adjusted to the desired sizes by appropriate measures e.g. the power and duration of an ultrasonic treatment. In this embodiment of the method according to the invention it is possible for example to incorporate liquid active substances such as perfume oils, pharmaceutically active oils, lipophilic solid active substances dissolved in oils or gas bubbles as contrast agents.

The method according to the invention also enables the production of capsules for enclosing active substances. The inner space can be loaded with molecules by varying the permeability of the shell as a function of the external physical and chemical parameters. A state of high permeability is adjusted for the loading. The enclosed material is subsequently retained by changing the external parameters or/and closing the pores for example by condensation of the shell or chemical or/and thermal modification of the pores or channels.

The precipitation method according to the invention allows charged or/and uncharged components to be deposited on the template particles. In a preferred embodiment of the invention the components required to form the shell contain at least one polyelectrolyte, for example two oppositely charged polyelectrolytes or/and a polyvalent metal cation and a negatively charged polyelectrolyte.

Polyelectrolytes are generally understood to mean polymers having ionically dissociable groups which may be a component or substituent of the polymer chain. The number of these ionically dissociable groups in the polyelectrolytes is usually large enough to ensure the water-solubility of the polymers in a dissociated form (also referred to as polyions). The term polyelectrolyte as used herein also refers to ionomers in which the concentration of the ionic groups is not sufficient to make them water soluble but they have sufficient charges for a self-assembly. The shell preferably contains "true" polyelectrolytes. Polyelectrolytes are divided into polyacids and polybases depending on the type of the dissociable groups. Polyanions which can be inorganic as well as organic polymers are formed from polyacids when they dissociate with cleavage of protons.

Polybases contain groups which are able to accept protons e.g. by reaction with acids to form salts. Polybases can have groups in the chains or side groups that are dissociable and form polycations by accepting protons.

Polyelectrolytes that are suitable according to the invention are biopolymers such as alginic acid, gum arabic, nucleic acids, pectins, proteins and other biopolymers that may be chemically modified such as ionic or ionizable polysaccharides e.g. carboxymethyl cellulose, chitosan and chitosan sulfate, lignin sulfonates and synthetic polymers such as polymethacrylic acid, polyvinylsulfonic acid, polyvinyl-phosphonic acid and polyethyleneimine.

Suitable polyanions include naturally occurring polyanions and synthetic polyanions. Examples of naturally occurring polyanions are alginate, carboxymethylamylose, carboxymethylcellulose, carboxymethyldextran, carageenan, cellulose sulfate, chrondroitin sulfate, chitosan sulfate, dextran sulfate, gum arabic, guar gum, gellan gum, heparin, hyaluronic acid, pectin, xanthan and proteins at an appropriate pH.

Examples of synthetic polyanions are polyacrylates (salts of polyacrylic acid), anions of polyamino acids and copolymers thereof, polymaleinate, polymethacrylate, polystyrene sulfate, polystyrene sulfonate, polyvinyl phosphate, polyvinyl phosphonate, polyvinyl sulfate, polyacrylamide methylpropane sulfonate, polylactate, poly(butadiene/maleinate), poly (ethylene/maleinate), poly (ethacrylate/acrylate) and poly (glyceryl methacrylate).

Suitable polybases include naturally occurring polycations and synthetic polycations. Examples of suitable naturally occurring polycations are chitosan, modified dextrans, e.g. diethylaminoethyl-modified dextrans, hydroxymethylcellulose trimethylamine, lysozyme, polylysine, protamine sulfate, hydroxyethylcellulose trimethylamine and proteins at appropriate pH values. Examples of synthetic polycations are polyallylamine, polyallylamine hydrochloride, polyamines, polyvinylbenzyl-trimethylammonium chloride, polybrene, polydiallyldimethylammonium chloride, polyethyleneimine, polyimidazoline, polyvinylamine, polyvinylpyridine, poly(acryl-amide/methacryloxypropyltrimethylammonium bromide), poly(diallyldimethyl-ammonium chloride/N-isopropylacrylamide), poly(dimethylaminoethyl-acrylate/acrylamide), polydimethylaminoethyl-methacrylate, polydimnethylamino-epichlorohydrin, polyethylenciminoepichlorohydrin, polymethacryloxyethyl-trimethylammonium bromide, hydroxypropylmethacryloxyethyldimethylammonium chloride, poly(methyldiethylaminoethylmethacrylate/acrylamide), poly(methyl/ guanidine), polymethylvinylpyridinium bromide, poly(vinylpyrrolidone/dimethyl-aminoethylmethacrylate) and polyvinylmethylpyridinium bromide.

Linear or branched polyelectrolytes can be used. The use of branched polyelectrolytes leads to less compact polyelectrolyte multifilms having a higher degree of wall porosity. The capsule stability can be increased by cross-linking polyelectrolyte molecules within or/and between the individual layers e.g. by cross-linking amino groups with aldehydes. It is also possible to use amphiphilic polyelectrolytes, e.g. amphiphilic block or random copolymers having a partial polyelectrolyte character to reduce permeability to small polar molecules. Such amphiphilic copolymers consist of units of different functionalities e.g. acidic or basic units on the one hand and hydrophobic units on the other hand such as styrenes, dienes or siloxanes etc. which can be arranged as blocks or randomly distributed over the polymer. The permeability or other properties of the capsule walls can be adjusted in a defined manner by using copolymers which change their structure as a function of the external conditions. These may for example be weak polyelectrolytes, polyampholytes or copolymers having a poly (N-isopropylacrylamide) component e.g. poly(N-isopropylacrylamideacrylic acid) which due to the equilibrium of hydrogen bridges, change their water solubility as a function of the temperature which is associated with swelling.

The release of the enclosed active substances can be regulated via the disintegration of the capsule walls by using polyelectrolytes that can be degraded under certain conditions e.g. photolabile, acid-labile, base-labile, salt-labile or thermolabile polyelectrolytes. Furthermore conductive polyelectrolytes or polyelectrolytes having optically active groups can be used as capsule components for special applications.

The properties and composition of the polyelectrolyte shell of the capsules according to the invention can be adjusted in a defined manner by suitable selection of the polyelectrolytes. The composition of the shells can be varied over a wide range by selection of substances for the layer structure. There are basically no limitations with regard to the polyelectrolytes or ionomers that are used provided the molecules have a sufficient charge or/and the ability to bind to the underlying layer by other types of interaction such as hydrogen bonds and/or hydrophobic interactions.

Hence suitable polyelectrolytes are low molecular polyelectrolytes or polyions and macromolecular polyelectrolytes such as polyelectrolytes of biological origin.

The permeability of the shell wall is of particular importance for the use of the capsules. As already stated above, the large number of polyelectrolytes that are available enables the production of numerous shell compositions having different properties. In particular the electric charge of the outer shell can be adapted to the intended use. Moreover the inner shell can be adapted to the encapsulated active substances which can for example lead to a stabilization of the active substance. Furthermore the permeability of the shell wall can be influenced by the selection of the polyelectrolytes in the shell and by the wall thickness as well as ambient conditions. This enables a selective design of the permeability properties and a defined change in these properties.

The permeability properties of the shell can be further modified by pores in at least one of the polyelectrolyte layers. Such pores can be formed by the polyelectrolytes themselves if a suitable choice is made. In addition to the polyelectrolytes, the shell can also contain other substances in order to achieve a desired permeability. Thus the permeability to polar components can be lowered by incorporating nanoparticles having anionic and/or cationic groups or surface-active substances such as surfactants or/and lipids. The incorporation of selective transport systems such as carriers or channels in the polyelectrolyte shell and in particular in lipid layers enables an exact adaptation of the transversal transport properties of the shell to the respective intended use. The pores or channels of the shell wall can be opened or closed in a specific manner by chemical modification or/and change of the ambient conditions. Thus for example a high salt concentration of the surrounding medium increases the permeability of the shell wall.

A first embodiment of the method according to the invention comprises a complex precipitation or coacervation of two oppositely charged polyelectrolytes from an alkaline solution in which they are both kept in solution simultaneously without reacting with one another. The template particles to be coated are added to this solution. Subsequently it is titrated with acid, e.g. HCl, into the neutral range which results in an encapsulation of the template particles. After separation of the encapsulated particles from the complexes in the free solution e.g. by filtration, centrifugation or sedimentation, the template particles can be dissolved if necessary.

In a further preferred embodiment the surface precipitation can occur from a solution containing a complex consisting of a low-molecular ion and an oppositely charged polyelectrolyte. Examples of suitable low-molecular ions are metal cations, inorganic anions such.as sulfate, carbonate, phosphate, nitrate etc., charged surfactants, charged lipids and charged oligomers in combination with an appropriate oppositely charged polyelectrolyte. A dispersed source for the one polyelectrolyte is generated in this process while the other polyelectrolyte is present at the same time. The polyelectrolyte of the complex can be the polycation as well as the polyanion. The choice depends on the template particles used and other conditions. In this embodiment a positively charged polyelectrolyte with a multiply negatively charged low-molecular anion e.g. sulfate is added to a solution of the negatively charged polyelectrolyte and a suspension of the template particles which results in a coating of the template particles. The coated template particles can for example be separated from the free complexes by centrifugation, filtration and subsequent washing and—provided they are soluble particles—be dissolved to produce microcapsules.

Another preferred embodiment comprises surface precipitation from a solution containing partially destabilized polyelectrolyte complexes (polycation/polyanion) by adding salt or/and pH variation. In this process there is a gradual transfer of polyelectrolytes from the complexes onto the template surface. This can be accomplished by introducing and stirring the negatively and positively charged polyelectrolyte in an aqueous solution having a high salt content preferably a salt content of $\geq 0.5$ mol/l, e.g. 1 M NaCl. The template particles are coated after addition to the solution. The coated template particles can for example be isolated by centrifugation or filtration and subsequent washing and optionally dissolved to generate microcapsules.

In another preferred embodiment the shell contains metal cations and at least one negatively charged polyelectrolyte. Divalent metal cations and in particular trivalent metal cations are for example used as metal cations. Examples of suitable metal cations are alkali earth metal cations, transition metal cations and rare earth element cations such as $Ca^{2+}$, $Mg^{2+}$, $Y^{3+}$, $Tb^{3+}$ and $Fe^{3+}$.

On the other hand it is also possible to use monovalent cations such as Ag+. Template particles coated with a metal layer can be produced by reducing the metal cations.

In still another preferred embodiment the components that are necessary to form the shell comprise at least one macromolecule e.g. an abiogenic macromolecule such as an organic polymer or a biomolecule such as a nucleic acid e.g. DNA, RNA or a nucleic acid analogue, a polypeptide, a glycoprotein or a polysaccharide having a molecular weight of preferably $\geq 5$ kD, and particularly preferably of $\geq 10$ kD. The macromolecules can carry charges such as nucleic acids or be uncharged such as polysaccharides e.g. dextran. The macromolecules can optionally be combined with polyelectrolytes or/and polyvalent metal cations in which case combinations of macromolecular and low-molecular biological cell substances, macromolecular and low-molecular abiogenic substances and macromolecular and biogenic and abiogenic substances can for example be used.

In yet a further preferred embodiment the components that are added to form the shell comprise a mixture of several polyelectrolytes or/and lipids or/and proteins or/and peptides or/and nucleic acids or/and other organic and inorganic compounds of biogenic or abiogenic origin. A suitable composition of the solvent with regard to salt content, pH value, cosolvents, surfactants and a suitable selection of the coating conditions e.g. temperature, rheological conditions, presence of electrical or/and magnetic fields, presence of light results in a self-assembly of the shell components on the templates to form complex structures having a wide variety of biomimetic properties.

Another preferred embodiment of the method is characterized in that contacting the liquid, salt-containing shell phase with the templates changes the system conditions in such a manner that, without any further external stimulation except for the permanent mixing, the shells are formed spontaneously and remain intact after an optional dissolution of the templates.

The precipitation according to step (b) of the method according to the invention occurs under conditions such that a shell of a defined thickness is formed around the template which is in the range of 1 to 100 nm, preferably 1 to 50 nm, particularly preferably 5 to 30 nm and most preferably 10 to 20 nm. The wall thickness and the homogeneity of the capsule shell are determined by the rate of polymer precipitation. This depends essentially on the concentration of the template particles, the concentration of the coating components and the rate of the solubility change in the liquid phase which causes the precipitation.

The precipitation can for example by carried out by firstly adding a part of the components forming the shell to the liquid phase and subsequently adding one or more additional shell components. Such a precipitation step can for example be used for a combination of metal cations and oppositely charged polyelectrolytes. Another method of precipitation is that the components required to form the shell are already completely present in the liquid phase and a change in the liquid phase occurs which results in the precipitation. This change in the liquid phase can for example be a change of the pH value and/or a change in the composition of the liquid phase e.g. by adding a solvent component or/and removing a solvent component. Thus for example hydrophilic biopolymers such as DNA or polysaccharides can be precipitated by adding ethanol to an aqueous liquid phase, whereas polyelectrolyte combinations can be precipitated by evaporating off an organic solvent such as acetone from the liquid phase.

The coating method according to the invention can additionally comprise at least one additional coating step before or/and after the precipitation step. Such an additional coating step can for example comprise the application of one or more lipid layers or/and the application of layers of polyelectrolytes.

The permeability of a shell can be modified by depositing lipid layers or/and amphiphilic polyelectrolytes on the polyelectrolyte shell. This can result in a very substantial reduction of the permeability of the shells to small and polar molecules. Examples of lipids that can be deposited on the shells are lipids which carry at least one ionic or ionogenic group e.g. phospholipids such as dipalmitoylphosphatidic acid or zwitterionic phospholipids such as dipalmitoylphosphatidyl choline or fatty acids or corresponding long chain alkylsulfonic acids. The use of zwitterionic lipids enables the deposition of lipid multilayers on the shell.

The application of polyelectrolytes in layers can for example be carried out as described in WO 99/47252. The layered assembly of the shells can for example be combined with the precipitation step according to the invention in such a manner that firstly a small number e.g. 1 to 4 layers of polyelectrolytes are layered onto the template particles which is followed by a precipitation step according to the invention. Alternatively or additionally it is also possible to deposit layers of polyelectrolytes on the shell after the precipitation steps.

Monodisperse capsules can be produced by the method according to the invention. Thus it is possible to obtain a composition having a capsule distribution in which the proportion of capsules whose deviation from the average diameter is >50%, less than 20%, preferably less than 10% and particularly preferably less than 1%.

The capsules are very stable towards chemical, biological, mechanical and thermal stress. The capsules containing the enclosed active substances can be optionally dried, frozen or/and freeze dried without affecting their properties. After thawing or resuspension in a solvent e.g. an aqueous solution, the intact capsules are obtained again under suitable media conditions or/and with an appropriate composition of the medium.

A powdery composition is obtained by drying or freeze-drying the capsules which can be resuspended in suitable solvents and in particular in aqueous solutions. The drying can be carried out by known methods in particular at an elevated or reduced temperature or/and reduced pressure.

The invention is further elucidated by the following figures and examples.

FIG. 6 shows a microscopic confocal picture of colloidal particles coated by precipitates of fluorescent-labelled dextran (a) and fluorescent-labelled DNA (b) on melamine-formaldehyde particles by the dropwise addition of ethanol to an aqueous suspension.

FIG. 7 shows empty shells consisting of the polyanion/metal complex PSS/Tb characterized by means of scanning force microscopy. A top view of a capsule consisting of 20 shell layers is shown in FIG. 7a and a top view of several capsules each consisting of about 100 shell layers is shown in FIG. 7b.

Figure 1:
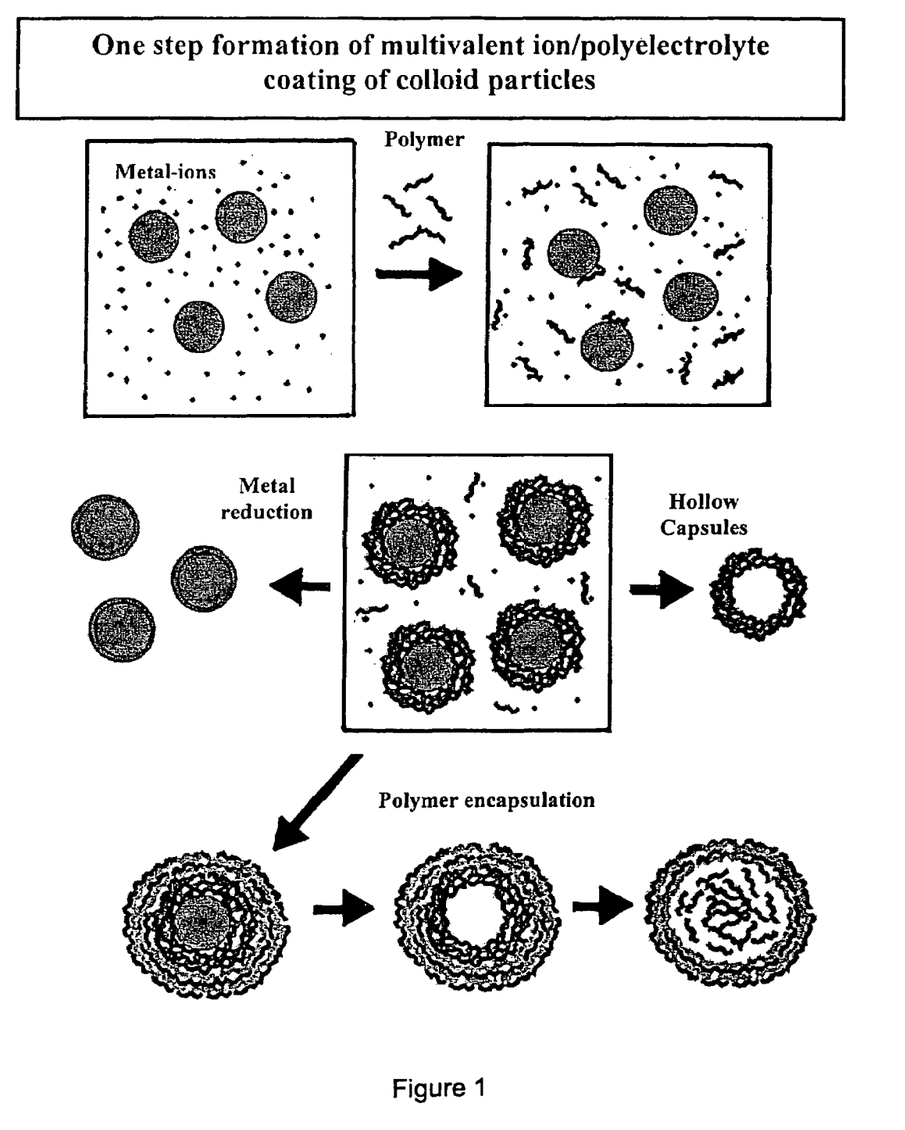
FIG. 1 shows an embodiment of the method according to the invention comprising a one step formation of a polyelectrolyte/ion shell on colloidal template particles.
Figure 2:
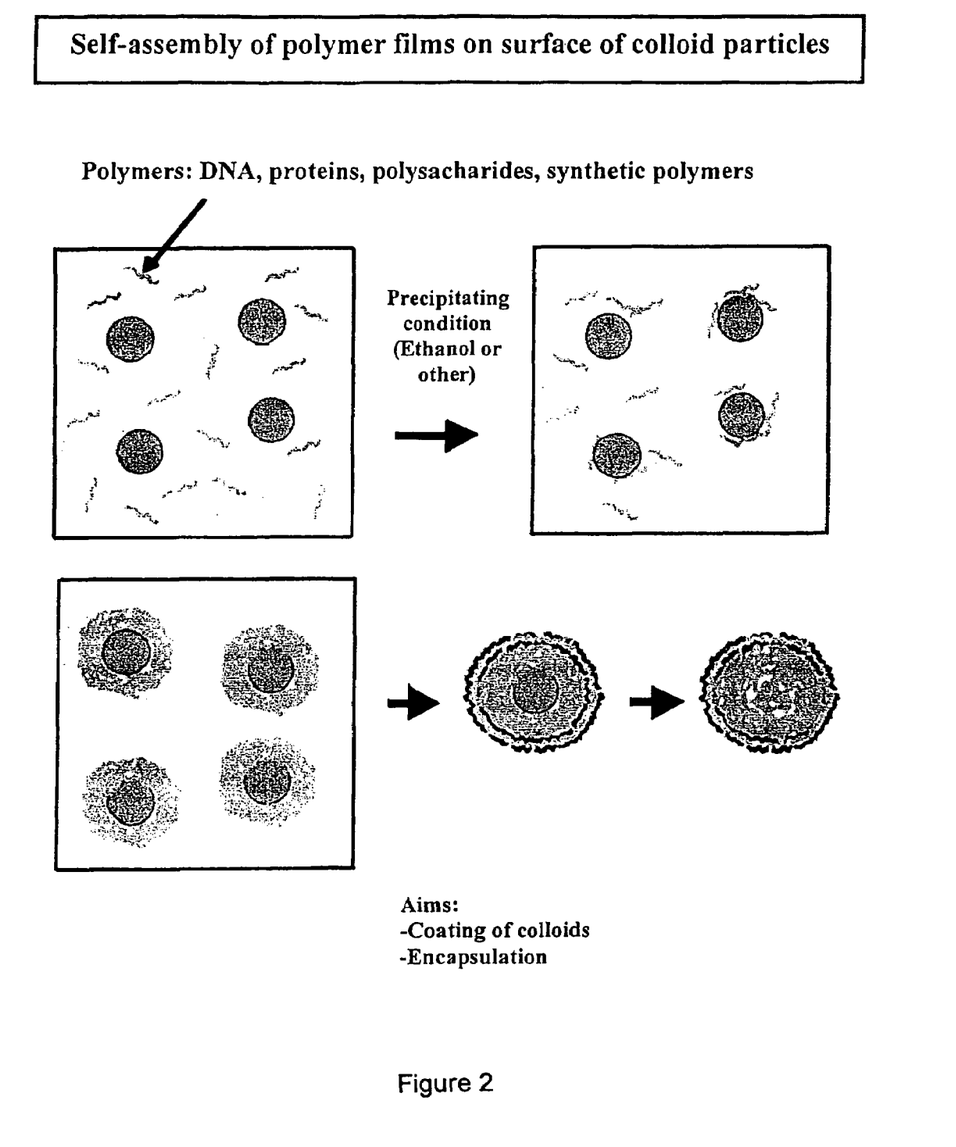
FIG. 2 shows another embodiment of the method according to the invention comprising a self-assembly of polymer films on the surface of colloidal particles.

FIGS. 1 and 2 show a schematic representation of two embodiments of the method according to the invention. In FIG. 1 a suspension of template particles (2) is produced which contains metal ions e.g. ions of a polyvalent metal or ions of a noble metal such as $Ag^+$ (4). An ion/polyelectrolyte shell is precipitated on the template particles by dropwise addition of a solution containing negatively charged polyelectrolyte molecules (6). The coated template particles (8) can be processed in various ways. Thus empty capsules (10) can be produced by dissolution of the template particles. Metal-coated capsules (12) are obtained by reducing the metal ions. By applying layers of oppositely charged polyelectrolytes (14a, 14b) it is possible to produce capsules with an anisotropic shell in which case the inner part is an ion/polyelectrolyte shell and the outer part is a polyelectrolyte/polyelectrolyte shell assembled in layers. Empty capsules (18) can be subsequently produced by dissolving the template particles. The inner ion/polyelectrolyte part of the shell can be dissolved by removing the metal ions (4) such that the polymer (6) is encapsulated in the interior of the shell formed (20) by the oppositely charged polyelectrolytes (14a, 14b).

Another embodiment of the method according to the invention is shown in FIG. 2. A suspension of colloidal template particles (32) is placed in a liquid phase which contains a polymer e.g. a nucleic acid, a protein, a polysaccharide or a synthetic polymer in a dissolved form. The polymer is precipitated to form template particles (36) coated with the polymer by changing the solvent composition e.g. by the dropwise addition of ethanol or another solvent in which the polymer is insoluble or only poorly soluble. Deposition of layers of oppositely charged polyelectrolytes (38a, 38b) allows the production of coated template particles with an anisotropic shell (40) where the inner section of the shell is formed by the precipitated polymer and the outer section is formed by layers of oppositely charged polyelectrolytes. If soluble template particles are used it is possible to dissolve them to form a polymer (42) encapsulated in the polyelectrolyte/polyelectrolyte shell.

EXAMPLES

Example 1

Preparation of PSS/PVBTAC Capsule Shells by One Step Precipitation 1.1 Materials Sodium polystyrene sulfate with a molecular weight of about 500,000 ($PSS^{500}$) and poly(vinylbenzyltrimethylammonium) chloride with a molecular weight of about 180,000 (PVBTAC) were obtained from Polysciences Europe GmbH. Sodium polystyrene sulfate with a molecular weight of about 70,000 ($PSS^{70}$) and poly(allylamine hydrochloride) with a molecular weight of 50 to 65,000 (PAH) were obtained from Aldrich.

Partly cross-linked monodispersed melamine-formaldehyde particles (MF-latex) with diameters of 5.2 and 10 μm were obtained from Microparticles GmbH, Berlin, Germany. These particles can be dissolved in acidic solutions of HCl (pH~1), sodium pyrosulfite solutions or organic solvents.

1.2 Methods 1.2.1. Layer Coating (Comparison)

The coating of template particles by membrane filtration was carried out as described by Voigt et al. (Ind. Eng. Chem. Res. 38 (1999), 4037). $PSS^{500}$ or PVBTAC adsorption (1 g/l in 0.5 M NaCl) and washing cycles were carried out alternately in a membrane filtration device (Millipore/Amicon ultrafiltration cell 8200 and Millipore membrane filter SSWP 090 25). Due to the negative charge of the MF latex, the adsorption of $PSS^{500}$ was started first. After adsorption of ten layers (5 layers each of $PSS^{500}$ and PVBTAC), the coated particles were pooled and suspended in a large volume of a HCl solution of pH 1. The suspension became transparent within a few seconds due to the decomposition of the MF latex template particles.

Microcapsules coated with layers were obtained in a ready-to-use form by membrane filtration after further washing steps.

1.2.2 Surface Precipitation (Invention)

The system $PSS^{500}$ (3 g/l/PVBTAC (1 g/l) in water (60% by weight)/acetone (20% by weight)/sodium bromide (20% by weight) behaves according to the phase diagram published by Michaels (Industrial Engineering Chemistry 57 (1965), 32) and Michaels et al. (J. Phys. Chem. 69 (1965), 1456), supra and yields a clear solution without detectable turbidity. 1 ml packed 5.2 μm MF latex particles (positively charged) corresponding to about 0.85 $m^2$ particle surface was added to 5 ml of this system. The solution window was left in two different ways i.e. by slowly evaporating acetone and by slowly adding water. The precipitation process was carried out for about 2 h at 20° C. Then the suspension was isolated and examined further.

1.2.3 Scanning Force Microscopy (SFM)

SFM images were obtained using a Digital Instrument Nanoscope IIIa. The sample was prepared by applying a drop of the microcapsule suspension to a clean mica surface and dried in air. The dried microcapsules were examined in the contact mode.

1.2.4 Confocal Laser Scanning Microscopy (CLSM)

Confocal images were obtained with the TCS SP confocal laser scanning microscope from Leica using an Aristoplan 100× oil immersion lens. 10 µl of the suspension of coated particles was placed on a microscope slide. 50 µl 0.1 mol/l HCl was added to this suspension. After 2 min a further 50 µl 0.1 mol/l NaOH was added. Small amounts of rhodamine 6G were added as a fluorescence marker for the capsule walls.

1.3 Results

Microcapsules prepared according to the prior art by deposition in layers had a typical ultrathin shell structure with a low wall thickness of about 15 nm. It was possible to completely dissolve these microcapsules by adding a ternary mixture of water/acetone/sodium bromide.

Figure 3:
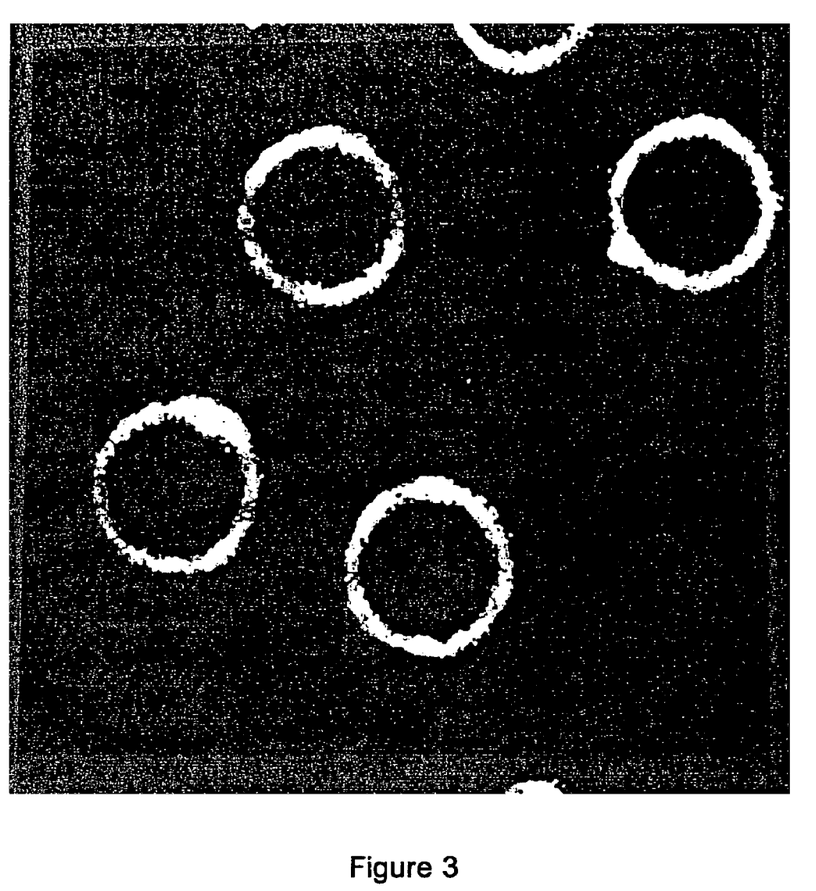
FIG. 3 shows a scanning microscopic confocal laser picture of microcapsules produced by a one step precipitation from the ternary mixture water/acetone/sodium bromide containing $PSS^{500}$ and PBVTAC. The template was a dissolvable melamine-formaldehyde latex particle of 5.2 μm in diameter. The solubility window was left by acetone evaporation.
Figure 4:
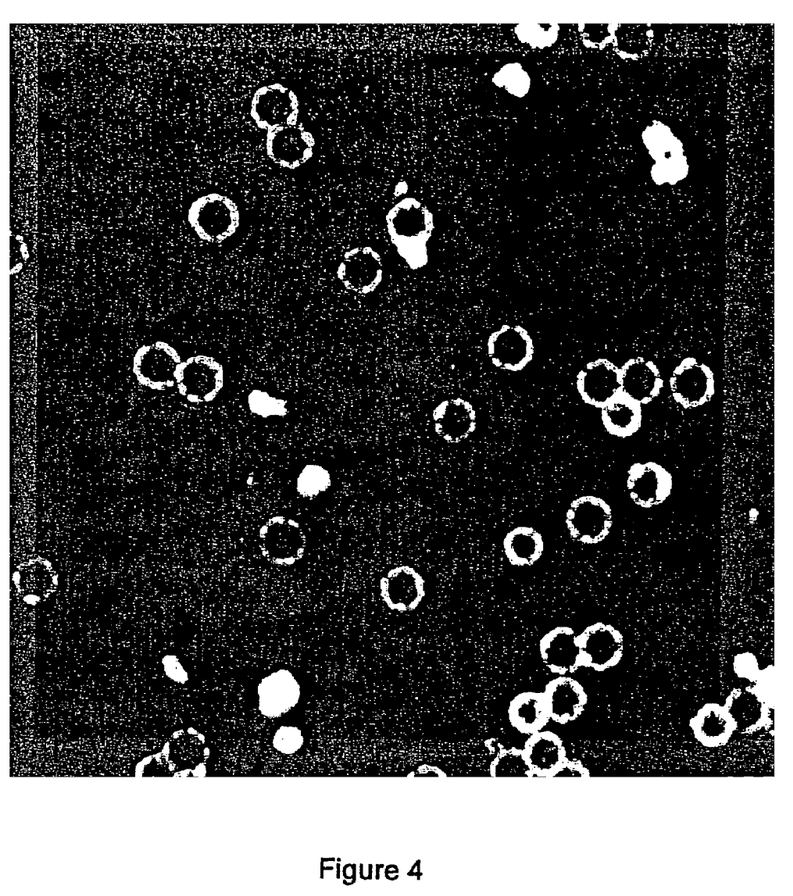
FIG. 4 shows a scanning microscopic confocal laser picture of microcapsules obtained by a one step method from the ternary mixture water/acetone/sodium bromide containing $PSS^{500}$ and PVBTAC. The template was a dissolvable melamine-formaldehyde latex particle of 5.2 μm in diameter. The solubility window was left by adding water.

CLSM images of capsules that were prepared by the one step surface precipitation according to the invention are shown in FIGS. 3 and 4. In FIG. 3 the solubility window was left by acetone evaporation and in FIG. 4 by adding water. The size and shape of the microcapsules are similar to those of the template particles. A large proportion of the microcapsules is somewhat smaller than the original template particles. An examination of the permeability properties showed that small polar dyes were able to penetrate the shell as was the case with the capsules prepared in the stepwise manner.

Example 2

Preparation of Polyelectrolyte/ion and Polymer Capsule Shells by One Step Precipitation 2.1 Materials PSS with a molecular weight of 70,000, PAH with a molecular weight of 50,000 and acridine orange (AO) were obtained from Aldrich. $Y(NO_3)_3$, $FeCl_3$ and $TbCl_3$ were obtained from Merck. Dipicolinic acid (DPA) and 4-pyrene sulfate (4-PS) were obtained from Molecular Probes. DNA and dextran (molecular weight 76,000) labelled with rhodamine (Rd) were obtained from Sigma.

Polystyrene latex particles (PS) modified with sulfate groups (diameter 468 nm) were prepared according to the method described by Furizava et al. (Kolloid-Z. Z. Polym, 250 (1972), 908). Dispersions of acid-soluble melamine-formaldehyde particles (MF-latex) with diameters of 4 to 6.5 µm were obtained from Microparticles GmbH, Berlin, Germany.

2.2 Methods

Confocal laser scanning microscopy and scanning force microscopy were carried out as described in example 1.

2.3 Results 2.3.1 Precipitation of Metal Ion/Polyelectrolyte Shells

A suspension of the MF latex particles was mixed with $Tb^{3+}$ ions. After adding the polyanion PSS, $Tb^{3+}$/PSS precipitates were formed. The suspension (1 ml) was stirred continuously while adding a PSS-Rd solution (1 mg/ml) in a dropwise manner (10 µl) until the PSS-Rd concentration reached a particular value (Table 1). After 10 to 15 min the particles were centrifuged and the portion of PSS-Rd molecules which were not bound to the particles was determined by measuring the fluorescence in the supernatant. Table 1 shows the data for the final concentration of MF particles, $Tb^{3+}$ ions and the concentration of PSS after addition to the suspension. It is remarkable that about 80 to 85% of the added PSS was adsorbed to the MF latex particles at all examined concentrations.

Figure 5:
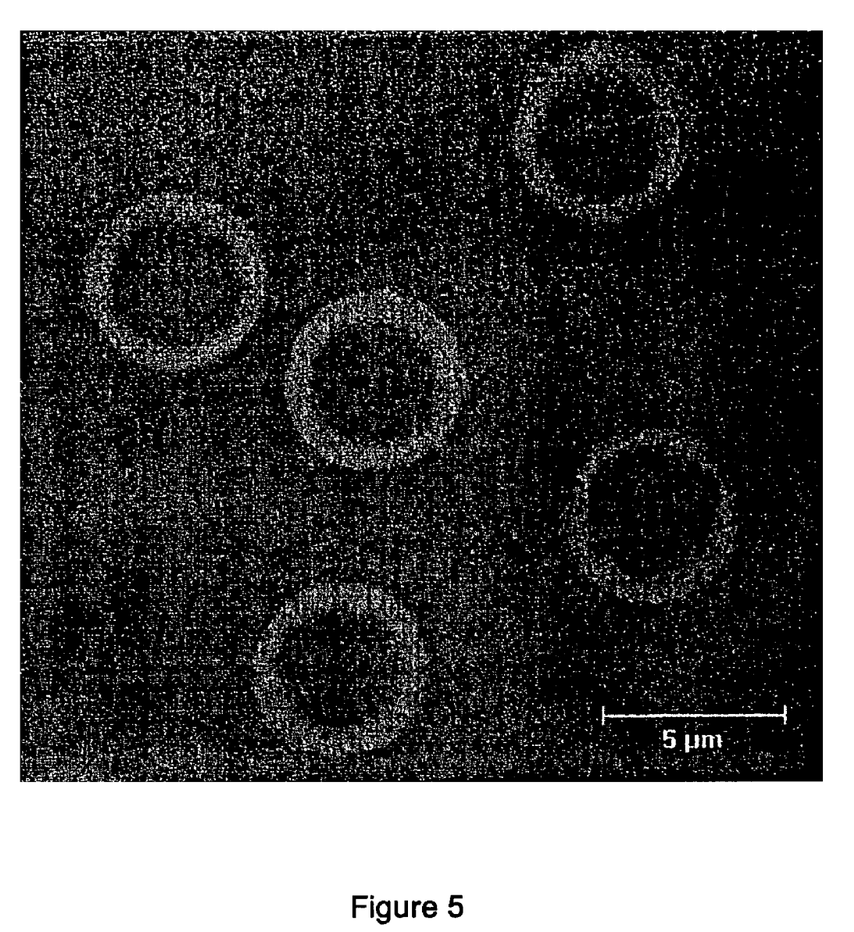
FIG. 5 shows a confocal microscopic picture of colloidal particles coated by fluorescent-labelled PSS and Tb ions.

The MF particles were examined by confocal microscopy. A typical picture of MF particles coated with PSS/$Tb^{3+}$ is shown in FIG. 5. The MF particles are uniformly covered with the fluorescent label. Almost no fluorescent label was found outside the particles.

TABLE 1

| Experiment | MF particle concentration | $TbCl_3$, M | PSS, monoM | supernatant, fluorescence % | estimated amount of PSS monolayers |
|---|---|---|---|---|---|
| 1 | $10^8$ cm$^{-3}$ | $10^{-3}$ | $2 \times 10^{-4}$ | 10 | 20 |
| 2 | $10^8$ cm$^{-3}$ | $10^{-3}$ | $10^{-3}$ | 15 | 80 |
| 3 | $10^8$ cm$^{-3}$ | $3 \times 10^{-3}$ | $3 \times 10^{-3}$ | 13 | 250 |

2.3.2 Precipitation of Polymer Shells

The controlled precipitation of polymers on the surface of colloid particles was achieved by reducing the solubility of polymers. DNA and dextran were used as polymers due to their low solubility in ethanol.

Firstly 1.5 ml of an MF latex particle suspension (particle concentration $5 \times 10^8$/cm$^{-3}$) was prepared with a DNA concentration of $3 \times 10^{14}$ molecules per cm$^3$. Then ethanol was added dropwise to the suspension to a volume of 4.5 ml. During this dropwise addition of ethanol the suspension was shaken. After 15 min the suspension was centrifuged. By determining the fluorescence (AO) in the supernatant it was found that about 20% of the DNA was not bound to the particles.

A similar experiment was also carried out using rhodamine-labelled dextran (dextran-Rd). For this purpose 1 ml of an MF latex particle suspension (concentration $5 \times 10^8$ particles per cm$^3$) and dextran-Rd ($3 \times 10^{15}$ molecules per cm$^3$) was prepared. After precipitation, about 5% of dextran was found in the supernatant.

Figure 6A:
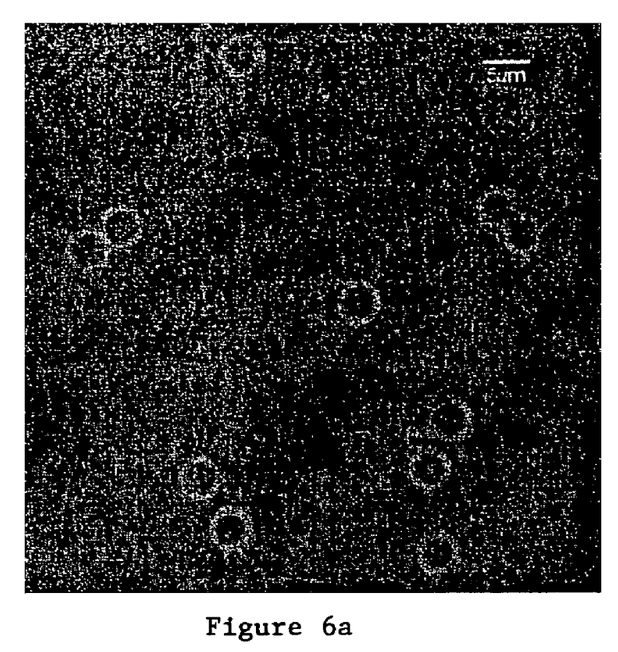
Figure 6B:
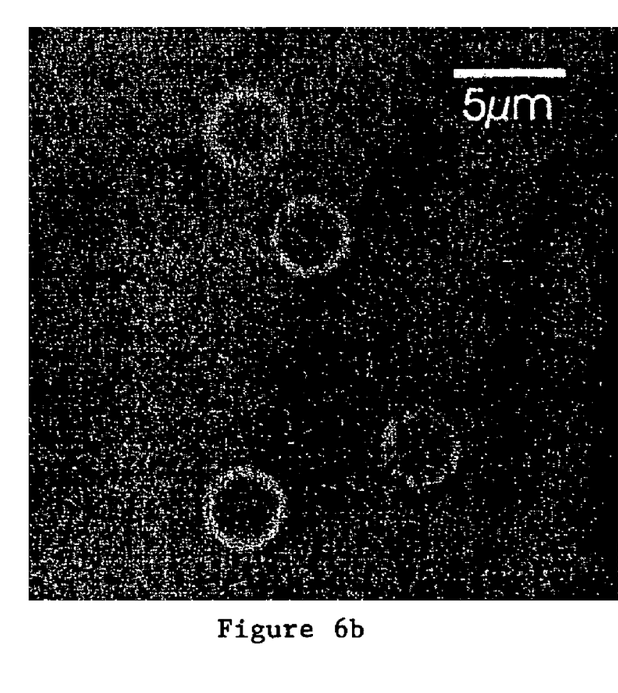

Typical fluorescence confocal microscope images are shown in FIGS. 6a and b. The pictures show that the fluorescent label is homogenous on the particle surface. An estimation of the average thickness of the polymer film on the particles yielded a value of about 50 monomolecular layers of DNA i.e. a thickness of about 100 nm.

2.3.3 Preparation of Empty Shells of Polyanion/metal Complexes

Figure 7A:
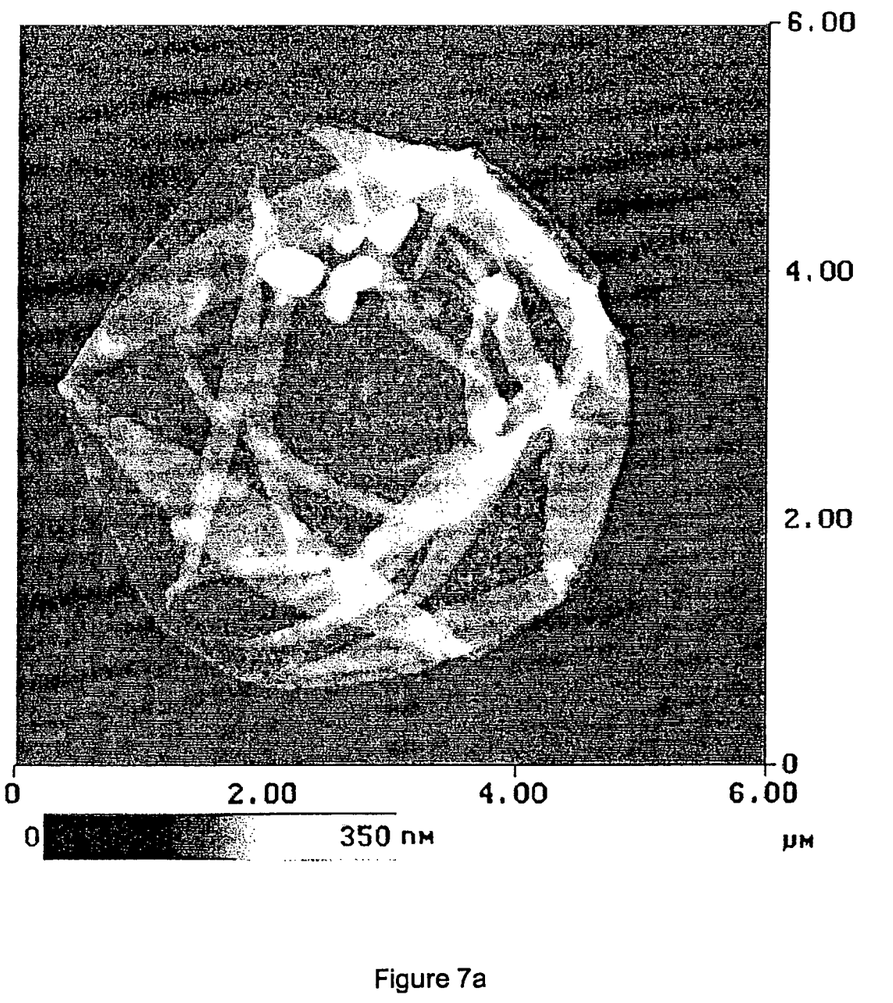

The Tb/PSS coated MF latex particles prepared in 2.3.1 were decomposed with 0.1 M HCl. The samples were examined by SFM. FIG. 7a shows a typical picture (top view) of a capsule of 20 monomolecular Tb/PSS layers. The spherical shape observed in solution by confocal microscopy changes after drying to a more polygonal shape. The average minimal height of the capsules obtained from several measuremehnts was about 20 nm.

Figure 7B:
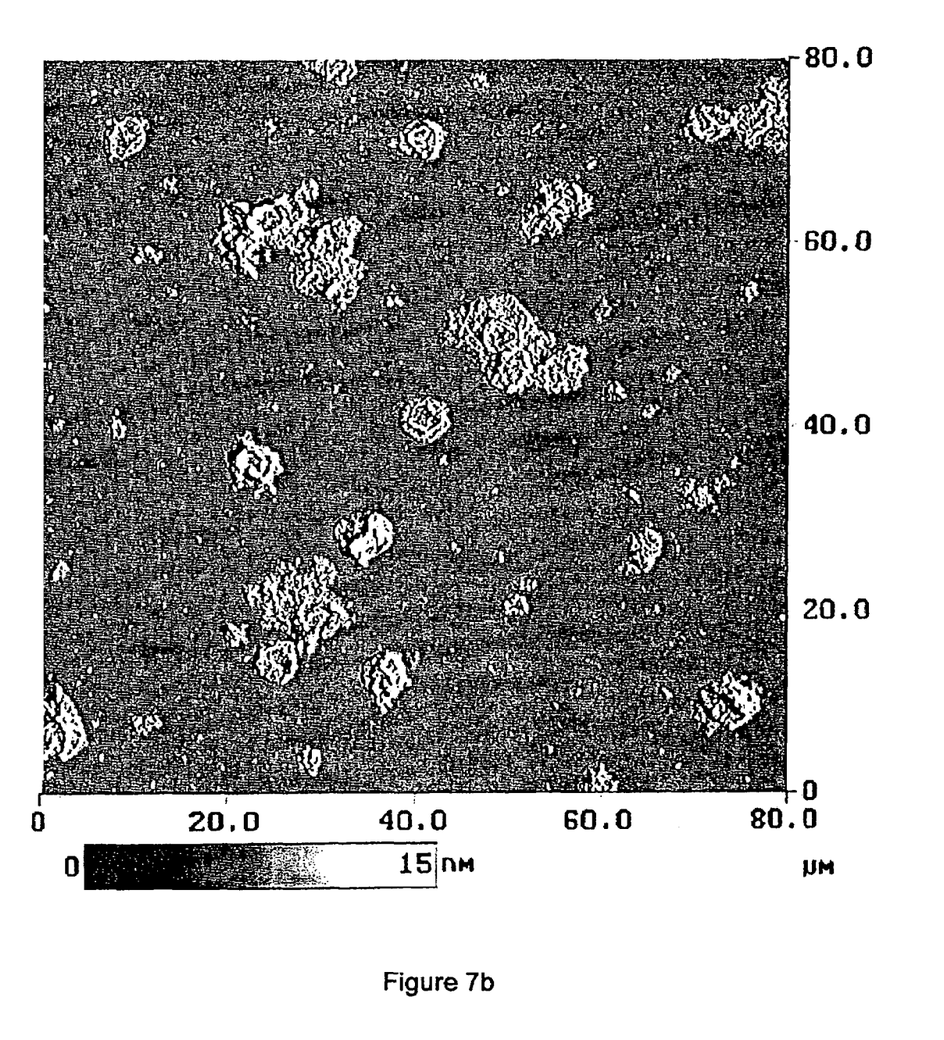

FIG. 7b shows a top view of an SFM picture of a sample containing several capsules consisting of about 100 monomolecular layers of Tb/PSS. Some of the capsules are broken. It is assumed that this low stability is due to the high thickness of the shell which reduces the permeability of the capsule. This leads to a higher osmotic pressure when the MF latex is dissolved and thus the capsules break more easily.

Example 3

Complex Precipitation or Coacervation from an Alkaline Solution of PSS and PAH A starting solution of the two polyelectrolytes was prepared in which the two were kept simultaneously in solution without reacting together (like the situation in the ternary solvent). This was achieved by firstly adding 10 ml 0.1% (w/w) NaOH solution containing 0.1 M NaCl. 15 mg PSS (MW 70,000) and 10 mg PAH (MW 50,000 to 65,000) were dissolved successively in this solution. It was shaken until complete dissolution (ca. 15 minutes). This solution is subsequently stable for several hours. 1 ml melamine-formaldehyde (MF) latex having a diameter of e.g. 4.7 μm was added. It was subsequently titrated into the neutral range using 1% (w/w) HCl. Microscopic control demonstrated the encapsulation of the MF cores. After separation of the encapsulated particles from the complexes in the free solution (e.g. filtration, centrifugation, sedimentation), dissolution of the MF cores in HCl solution of pH 1 within a short period (from about a few seconds to several minutes) resulted in the desired microcapsules.

The solubility conditions for both partners, regarded separately, were improved by adding acid. However, their mutual presence then resulted in less soluble complexes.

Example 4

Complex Precipitation or Coacervation from an Alkaline PSS/PAH Solution Containing Emulsion Droplets as the Template A starting solution of the two polyelectrolytes was prepared in which the two were kept simultaneously in solution without reacting together. This was achieved by firstly adding 100 ml 0.1% (w/w) NaOH solution containing 0.1 M NaCl. 300 mg PSS (MW 70,000) and 200 mg PAH (MW 50,000 to 65,000) were dissolved successively in this solution. It was shaken until complete dissolution. This solution is subsequently stable for several hours. 20 ml perfume oil was added. It was subsequently emulsified with an Ultra-Turrax and then rapidly titrated into the neutral range with 10% (w/w) HCl. Subsequently the emulsion was purified e.g. washed several times in a separating funnel. This resulted in an emulsion which is stable for several months.

Example 5

Surface Precipitation from a Solution Containing a Complex of Polyelectrolyte and Low-molecular Ligands and the Corresponding Oppositely Charged Polyelectrolyte Solution I: 0.5 ml PAH solution (MW 50,000–65,000, 1 mg/ml) containing NaCl (0.01–100 mM) +750 μl sodium sulfate solution ($10^{-2}$ M); solution II: 0.5 ml PSS (MW 70,000, 5 mg/ml) +10 μl melamine-formaldehyde template particles with a diameter of 6.1 μm. Solution II is added to solution I and stirred. After about 1 hour the system is purified (separation of the coated templates from the free complexes by means of centrifugation or filtration with subsequent washes). The template particles are dissolved by transferring them to a HCl solution of pH 1 and the microcapsules are obtained by additional purification steps.

Example 6

Surface Precipitation from a Solution Containing Partially Destabilized Polyelectrolyte Complexes (polycation/polyanion) by Adding Salt and/or Varying the pH 20 mg PSS and 10 mg PAH are added to 10 ml 1 M NaCl. The system is stirred for 10 minutes. Subsequently 1 ml MF latex of 4.7 μm is added. The system is stirred for several hours. Afterwards it is purified and washed, respectively, by centrifugation or filtration and the template is dissolved in dilute HCl (pH~1) and the capsules are isolated.

20 mg PAH and 10 mg PSS are added to 10 ml water and after the complex formation 10 ml 1 M NaCl is added. 1 ml MF latex of 4.7 μm is added. The system is stirred for several hours. Afterwards it is purified and washed, respectively, by centrifugation or filtration and the template is dissolved in dilute HCl (pH~1) and the capsules are isolated.

Example 7

One Step Precipitation from a Solution Containing a Complex of a Polyelectrolyte and a Multivalent Ion Solution I: 1 ml PSS solution (2 mg/ml) is admixed with 200 μl of a $Y(NO_3)_3$ solution ($2 \times 10^{-2}$ M). The resulting charge ratio between sulfate and yttrium is 5:3.

Solution II: 400 μl oil is mixed with 1 ml water. The mixture is emulsified with ultrasound for 3 to 4 minutes in an Ultra-Turrax.

Solution I is subsequently added rapidly to solution II and the resulting emulsion is shaken in a vortex for 2 minutes. The emulsion is stable for more than 20 hours and can be used as the starting system for further coatings if required.

The method according to the invention can be used universally. The physicochemical conditions of the medium are adjusted such that the preformed or/and the newly formed polyelectrolyte complexes are unstable in the shell liquid e.g. due to a high salt content. Surprisingly it turned out that a distribution of the polyelectrolytes over all compartments involved occurs in a finite time and that this can be controlled by suitable parameters. These of course also include the phase boundary of particle/medium or oil/medium. The polyelectrolytes can arrange themselves here in the known three-dimensional network structure containing more or less water. They can be converted into another configuration by after-treatment e.g. in aqueous solutions of high salt contents. For example an inadequately cross-linked shell can be converted into a more strongly cross-linked shell. It is also possible to generate structures near to the thermodynamic equilibrium as well as those which are due to adaptations to the given disequilibrium situations.

The invention claimed is:

1. Method for applying a shell to template particles comprising the steps:
   (a) providing a dispersion of template particles of suitable size in a salt-containing liquid phase which contains the components required to form the shell in a dissolved form and
   (b) precipitating the components from the liquid phase onto the template particles under conditions which enable the formation of a shell around the template particles that has a thickness of from 1 to 100 nm, wherein the components required to form the shell comprise
      (i) two oppositely charged polyelectrolytes,
      (ii) a polyvalent low-molecular cation and a negatively charged polyelectrolyte or
      (iii) a polyvalent low-molecular anion and a positively charged polyelectrolyte.

2. The method of claim 1 wherein the template particles are selected from solid, liquid, liquid-crystalline and gaseous particles.

3. The method of claim 1 wherein the template particles are selected from particles having a diameter of up to 50 μm.

4. The method of claim 1 wherein the template particles contain an active substance.

5. The method of claim 4 wherein the active substance is a catalyst selected from the group consisting of enzymes, nanoparticles, pharmaceutical agents, sensor molecules, crystals, polymers and gases.

6. The method of claim 1 wherein hollow cell wall particles obtainable from yeasts or other monocellular or multicellular living organisms containing cell walls or hollow pollen wall particles are used as templates.

7. The method of claim 1 wherein soluble particles are used as template particles.

8. The method of claim 7 wherein partly cross-linked melamine-formaldehyde particles, biological particles or cells are used as the soluble particles.

9. The method of claim 1 wherein the components required to form the shell comprise a divalent or trivalent low-molecular cation and a negatively charged polyelectrolyte.

10. The method of claim 1 wherein the components required to form the shell comprise a divalent or trivalent low-molecular anion and a positively charged polyelectrolyte.

11. The method of claim 1 wherein the components required to form the shell comprise at least one macromolecule.

12. The method of claim 11 wherein a biopolymer is used.

13. The method of claim 11 wherein a mixture of macromolecular and low-molecular biological cell substances is used.

14. The method of claim 11 wherein a mixture of macromolecular and low-molecular abiogenic substances is used.

15. The method of claim 11 wherein a mixture of macromolecular and low-molecular biogenic and abiogenic substances is used.

16. The method of claim 1 wherein the precipitation according to step
    (b) comprises adding a component of the shell to the liquid phase.

17. The method of claim 1 wherein the precipitation according to step (b) comprises a change in the liquid phase which results in the precipitation of the components of the shell.

18. The method of claim 17 wherein the change in the liquid phase comprises a change of the pH value or/and a change in the composition of the liquid phase.

19. The method of claim 1 wherein the system conditions are changed by bringing together the liquid salt-containing shell phase and the templates in such a manner that the shells are formed spontaneously without further external stimulation with the exception of permanent mixing and remain intact after optional dissolution of the templates.

20. The method of claim 1 additionally comprising at least one additional coating step before or/and after the precipitation step.

21. The method of claim 20 wherein the additional coating step comprises the application of a lipid layer or/and the application of a polyelectrolyte in layers.

22. The method of claim 1 additionally comprising the disintegration of soluble template particles.

23. The method of claim 1 additionally comprising an at least partial disintegration of the shell.

24. The method of claim 1 wherein a shell is formed around the template particles which has a thickness of 1 to 50 nm.

25. The method of claim 1 wherein a shell is formed around the template particles which has a thickness of 5 to 30 nm.

26. The method of claim 3, wherein the template particles are selected from particles having a diameter of up to 10 μm.

* * * * *